(12) United States Patent
Pourjafar et al.

(10) Patent No.: US 11,723,386 B2
(45) Date of Patent: Aug. 15, 2023

(54) CONTROLLING SUB-ACUTE RUMINAL ACIDOSIS IN A DAIRY COW

(71) Applicants: Amir Pourjafar, Shiraz (IR); Seyed Aliakbar Safavi, Shiraz (IR); Seyedbehnam Beladi, Shiraz (IR)

(72) Inventors: Amir Pourjafar, Shiraz (IR); Seyed Aliakbar Safavi, Shiraz (IR); Seyedbehnam Beladi, Shiraz (IR)

(*) Notice: Subject to any disclaimer, the term of this patent is extended or adjusted under 35 U.S.C. 154(b) by 891 days.

(21) Appl. No.: 16/597,890

(22) Filed: Oct. 10, 2019

(65) Prior Publication Data

US 2020/0041448 A1 Feb. 6, 2020

Related U.S. Application Data

(60) Provisional application No. 62/743,578, filed on Oct. 10, 2018.

(51) Int. Cl.
*A23K 50/10* (2016.01)
*A23K 20/20* (2016.01)
*A61B 5/145* (2006.01)

(52) U.S. Cl.
CPC .............. *A23K 50/10* (2016.05); *A23K 20/20* (2016.05); *A61B 5/14507* (2013.01)

(58) Field of Classification Search
CPC ..... A23K 50/10; A23K 20/20; A61B 5/14507
See application file for complete search history.

(56) References Cited

U.S. PATENT DOCUMENTS 6,694,161 B2 * 2/2004 Mehrotra ........... A61B 5/14539
600/300
10,349,627 B2 * 7/2019 Sato .................... A61B 5/14539

FOREIGN PATENT DOCUMENTS

CN 102068454 B * 4/2012
NL 1015120 C2 * 11/2001 ............. A01K 29/00

* cited by examiner

*Primary Examiner* — Navin Natnithithadha
*Assistant Examiner* — Meghan R Kumar
(74) *Attorney, Agent, or Firm* — Bajwa IP Law Firm; Haris Zaheer Bajwa (57) ABSTRACT

A method for controlling sub-acute ruminal acidosis (SARA) in a dairy cow. The method includes placing a pH sensor in a rumen of the dairy cow, obtaining pH data of the rumen utilizing the pH sensor, receiving the pH data by one or more processors, calculating a first average of the pH data and a second average of the pH data utilizing the one or more processors, generating a plurality of pH classes based on a plurality of predefined pH ranges, generating a plurality of sodium bicarbonate classes based on a plurality of predefined sodium bicarbonate mass ranges, designing a fuzzy control system based on a set of rules, and determining an amount of sodium bicarbonate to add to a water supply of the dairy cow utilizing the fuzzy control system based on the first average and the second average.

15 Claims, 7 Drawing Sheets

CONTROLLING SUB-ACUTE RUMINAL ACIDOSIS IN A DAIRY COW

CROSS-REFERENCE TO RELATED APPLICATION

This application claims the benefit of priority from U.S. Provisional Patent Application Ser. No. 62/743,578, filed on Oct. 10, 2018, and entitled "MONITORING, ASSESSMENT AND TELEMETRIC CONTROL OF (SARA) IN HIGH YIELDING DAIRY CATTLE," which is incorporated herein by reference in its entirety.

TECHNICAL FIELD

The present disclosure generally relates to control systems, and particularly, to fuzzy control systems.

BACKGROUND

Subacute Ruminal Acidosis (SARA) is a common and economically important problem in well managed dairy herds. SARA is generally a consequence of feeding high grain diets to dairy cows, which are adapted to digesting predominantly forage diets. Numerous methods are proposed for diagnosis of SARA based on impacts of SARA on ruminal pH. However, current methods may rely on manual diagnosis of ruminal pH which may have to be performed by an expert. There is, therefore, a need for a method for SARA diagnosis by quantifying impact of SARA on ruminal pH. There is also a need for a system for monitoring SARA based on variations of ruminal pH.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for controlling sub-acute ruminal acidosis (SARA) in a dairy cow. An exemplary method may include placing a pH sensor in a rumen of the dairy cow, obtaining pH data of the rumen utilizing the pH sensor, receiving the pH data by one or more processors, calculating a first average of the pH data and a second average of the pH data utilizing the one or more processors, generating a plurality of pH classes based on a plurality of predefined pH ranges, generating a plurality of sodium bicarbonate classes based on a plurality of predefined sodium bicarbonate mass ranges, designing a fuzzy control system based on a set of rules, and determining an amount of sodium bicarbonate to add to a water supply of the dairy cow utilizing the fuzzy control system based on the first average and the second average. In an exemplary embodiment, each of the plurality of pH classes may correspond to a respective predefined pH range of the plurality of predefined pH ranges and each of the plurality of sodium bicarbonate classes may correspond to a respective predefined sodium bicarbonate mass range of the plurality of predefined sodium bicarbonate mass ranges. In an exemplary embodiment, the fuzzy control system may include a first input, a second input, and an output.

In an exemplary embodiment, the first average may be associated with a first period of time and the second average may be associated with a second period of time. In an exemplary embodiment, the first period of time may include an about 24 hour period. In an exemplary embodiment, the second period of time may include an about 5 hour period.

In an exemplary embodiment, the set of rules may include mapping a pair of pH classes to a respective sodium bicarbonate class of the plurality of sodium bicarbonate classes. In an exemplary embodiment, the pair of pH classes may include a first pH class of the plurality of pH classes and a second pH class of the plurality of pH classes. In an exemplary embodiment, the first pH class may be associated with the first average and the second pH class may be associated with the second average.

In an exemplary embodiment, generating the plurality of pH classes may include generating a normal pH class (N) corresponding to a first predefined pH range of the plurality of predefined pH ranges, generating an ordinary pH class (O) corresponding to a second predefined pH range of the plurality of predefined pH ranges, generating a pretty low pH class (PL) corresponding to a third predefined pH range of the plurality of predefined pH ranges, generating a very low pH class (VL) corresponding to a fourth predefined pH range of the plurality of predefined pH ranges, and generating a critically low pH class (CL) corresponding to a fifth predefined pH range of the plurality of predefined pH ranges. In an exemplary embodiment, the first predefined pH range may include pH values larger than 6. In an exemplary embodiment, the second predefined pH range may include pH values between 5.7 and 6. In an exemplary embodiment, the third predefined pH range may include pH values between 5.5 and 5.7. In an exemplary embodiment, the fourth predefined pH range may include pH values between 5 and 5.5. In an exemplary embodiment, the fifth predefined pH range may include pH values smaller than 5.

In an exemplary embodiment, generating the plurality of sodium bicarbonate classes may include generating a zero sodium bicarbonate class (Z) corresponding to a first predefined sodium bicarbonate mass range of the plurality of predefined sodium bicarbonate mass ranges, generating a low sodium bicarbonate class (L) corresponding to a second predefined sodium bicarbonate mass range of the plurality of predefined sodium bicarbonate mass ranges, generating a medium sodium bicarbonate class (M) corresponding to a third predefined sodium bicarbonate mass range of the plurality of predefined sodium bicarbonate mass ranges, generating a high sodium bicarbonate class (H) corresponding to a fourth predefined sodium bicarbonate mass range of the plurality of predefined sodium bicarbonate mass ranges, and generating a very high sodium bicarbonate class (VH) corresponding to a fifth predefined sodium bicarbonate mass range of the plurality of predefined sodium bicarbonate mass ranges. In an exemplary embodiment, the first predefined sodium bicarbonate mass range may include zero grams of sodium bicarbonate. In an exemplary embodiment, the second predefined sodium bicarbonate mass range may include values between 120 gr and 150 gr of sodium bicarbonate. In an exemplary embodiment, the third predefined sodium bicarbonate mass range may include values between 150 gr and 175 gr of sodium bicarbonate. In an exemplary embodiment, the fourth predefined sodium bicarbonate mass range may include values between 175 gr and 187 gr of sodium bicarbonate. In an exemplary embodiment, the fifth predefined sodium bicarbonate mass range may include values between 187 gr and 200 gr of sodium bicarbonate.

In an exemplary embodiment, mapping the pair of pH classes to the respective sodium bicarbonate class may include mapping a pair of CL and CL to VH, mapping a pair of CL and VL to VH, mapping a pair of CL and PL to H, mapping a pair of CL and O to M, mapping a pair of CL and N to M, mapping a pair of VL and CL to VH, mapping a pair of VL and VL to H, mapping a pair of VL and PL to M, mapping a pair of VL and O to M, mapping a pair of VL and N to L, mapping a pair of PL and CL to H, mapping a pair of PL and VL to M, mapping a pair of PL and PL to M, mapping a pair of PL and O to L, mapping a pair of PL and N to L, mapping a pair of O and CL to M, mapping a pair of O and VL to L, mapping a pair of O and PL to L, mapping a pair of O and O to L, mapping a pair of O and N to Z, mapping a pair of N and CL to L, mapping a pair of N and VL to Z, mapping a pair of N and PL to Z, mapping a pair of N and O to Z, and mapping a pair of N and N to Z.

In an exemplary embodiment, designing the fuzzy control system may include generating a first input membership function for the first pH class, generating a second input membership function for the second pH class, and generating an output membership function for each of the plurality of sodium bicarbonate classes. In an exemplary embodiment, the first input membership function may be associated with the first input and the second input membership function may be associated with the second input. In an exemplary embodiment, the output membership function may be associated with the output. In an exemplary embodiment, each of the first input membership function, the second input membership function, and the output membership function may include a trapezoidal shape.

In an exemplary embodiment, determining the amount of sodium bicarbonate may include loading the first average to the first input of the fuzzy control system, loading the second average to the second input of the fuzzy control system, and determining the amount of sodium bicarbonate by obtaining the output of the fuzzy control system.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for controlling sub-acute ruminal acidosis (SARA) in a dairy cow. An exemplary method may include continuously measuring ruminal pH of a dairy cow and calculating average values of ruminal pH. Based on average pH values, an exemplary method may determine a level of ruminal acidosis and may estimate appropriate amount of sodium bicarbonate to be fed to the dairy cow to compensate SARA. An exemplary method may utilize a fuzzy control system for estimating a proper amount of sodium bicarbonate. An exemplary fuzzy control system may employ a predefined set of rules that map different ranges of ruminal pH to respective amounts of sodium bicarbonate.

Figure 1A:
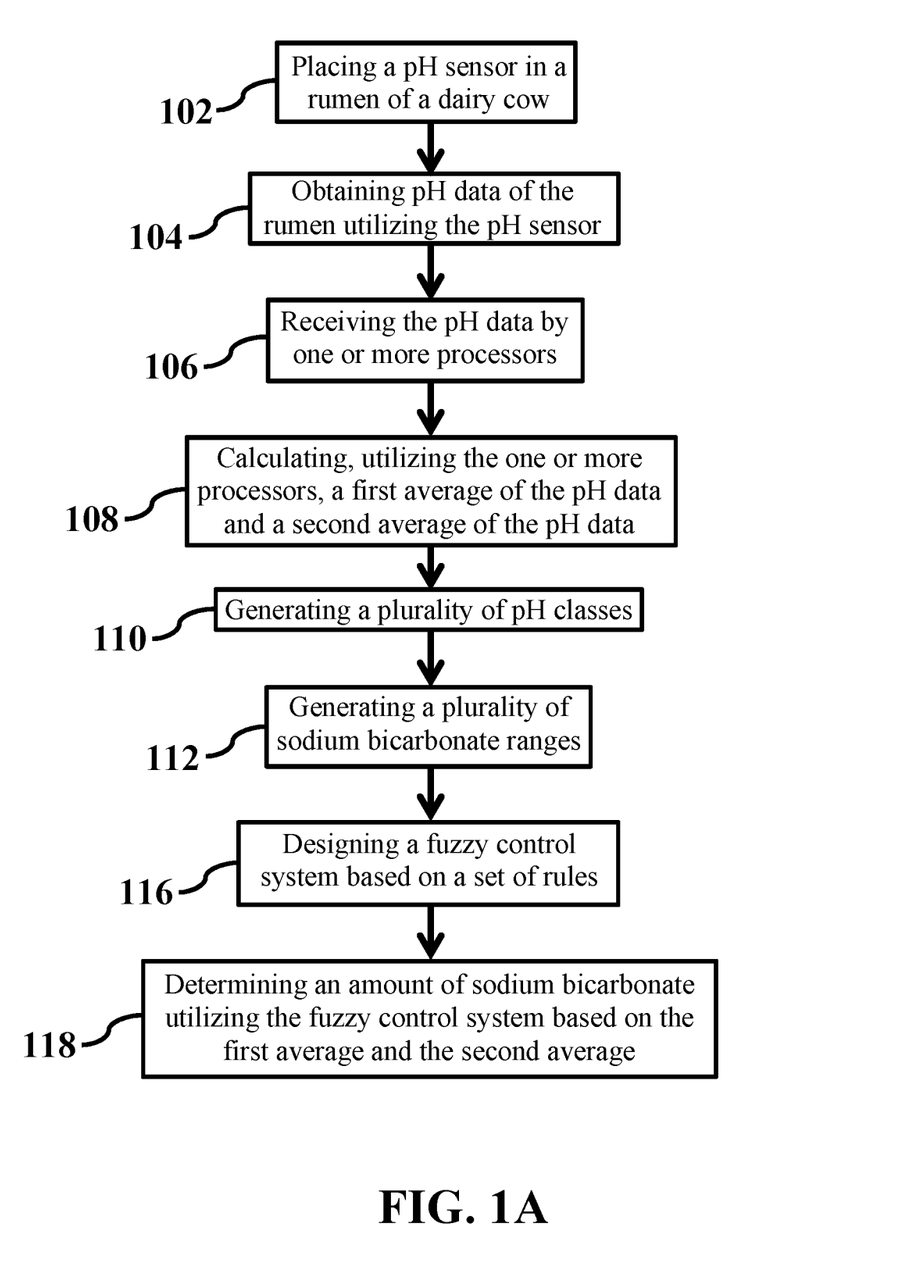
FIG. 1A shows a flowchart of a method for controlling sub-acute ruminal acidosis (SARA) in a dairy cow, consistent with one or more exemplary embodiments of the present disclosure.

FIG. 1A shows a flowchart of a method for controlling SARA in a dairy cow, consistent with one or more exemplary embodiments of the present disclosure. An exemplary method 100 may include placing a pH sensor in a rumen of the dairy cow (step 102), obtaining pH data of the rumen utilizing the pH sensor (step 104), receiving the pH data by one or more processors (step 106), calculating a first average of the pH data and a second average of the pH data utilizing the one or more processors (step 108), generating a plurality of pH classes (step 110) based on a plurality of predefined pH ranges, generating a plurality of sodium bicarbonate classes based on a plurality of predefined sodium bicarbonate mass ranges (step 112), designing a fuzzy control system based on a set of rules (step 116), and determining an amount of sodium bicarbonate sodium to add to a water supply of the dairy cow utilizing the fuzzy control system based on the first average and the second average (step 118). In an exemplary embodiment, the first average may be associated with a first period of time and the second average may be associated with a second period of time. In an exemplary embodiment, each of the plurality of pH classes may correspond to a respective predefined pH range of the plurality of predefined pH ranges. In an exemplary embodiment, each of the plurality of sodium bicarbonate classes may correspond to a respective predefined sodium bicarbonate mass range of the plurality of predefined sodium bicarbonate mass ranges.

Figure 2:
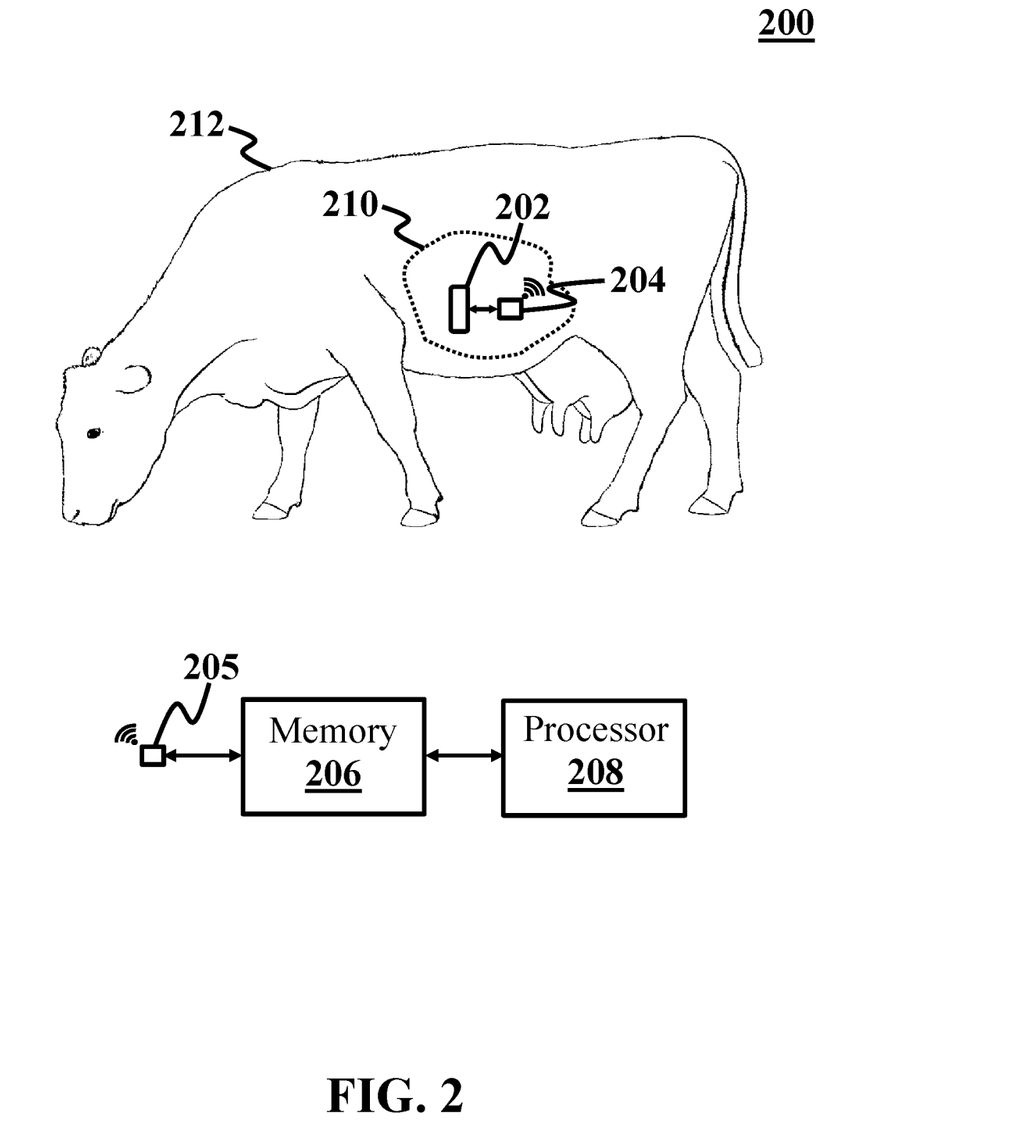
FIG. 2 shows a schematic of a system for controlling SARA in a dairy cow, consistent with one or more exemplary embodiments of the present disclosure.

FIG. 2 shows a schematic of a system for controlling SARA in a dairy cow, consistent with one or more exemplary embodiments of the present disclosure. In an exemplary embodiment, different steps of method 100 may be implemented by utilizing an exemplary system 200. An exemplary system 200 may include a pH sensor 202, a transmitter 204, a receiver 205, a memory 206, and a processor 208. In an exemplary embodiment, more than one processor may be utilized in system 200. In an exemplary embodiment, pH sensor 202 may be placed in a rumen 210 of a dairy cow 212, and transmitter 204 may be coupled with pH sensor 202. In an exemplary embodiment, memory 206 may have processor-readable instructions stored therein. In an exemplary embodiment, processor 208 may be configured to access memory 206 and execute the processor-readable instructions, which, when executed by processor 208 may configure processor 208 to perform different steps of method 100. In an exemplary embodiment, components of system 200 may be combined with one another or additional components may exist. Exemplary components are illustrative of functionality.

For further detail with respect to step 102, in an exemplary embodiment, placing pH sensor 202 in rumen 210 of dairy cow 212 may include making dairy cow 212 swallow pH sensor 202. For further detail with regards to step 104, pH sensor 202 may obtain the pH data by continuously measuring the pH of rumen 210.

In further detail with regards to step 106, pH sensor 202 may send the pH data to processor 208 by transmitting the pH data to receiver 205 via transmitter 204. In an exemplary embodiment, transmitter 204 may include a wireless or a Bluetooth transmitter and may be embedded inside pH sensor 202. In an exemplary embodiment, receiver 205 may include a wireless or a Bluetooth receiver and may be configured to receive the pH data from transmitter 204. In an exemplary embodiment, memory 206 may be configured to receive and store the pH data from receiver 205. By accessing the pH data on memory 206, processor 208 may utilize the pH data for implementing different steps of method 100.

In further detail with regards to step 108, in an exemplary embodiment, the first average of the pH data may be calculated for a time interval equal to the first period of time and the second average of the pH data may be calculated for a time interval equal to the second period of time. For example, the first period of time may include an about 24 hour period and the second period of time may include an about 5 hour period. Other time periods may also be utilized for average calculation. In an exemplary embodiment, processor 208 may utilize the captured pH data that may be stored in memory 206 during the first period of time and the second period of time to calculate the first average and the second average, respectively.

For further detail with regards to step 110, an exemplary plurality of pH classes may include a normal pH class, an ordinary pH class, a pretty low pH class, a very low pH class, and a critically low pH class. In an exemplary embodiment, the normal pH class may be referred to as "N" and may correspond to a first predefined pH range of the plurality of predefined pH ranges. In an exemplary embodiment, the ordinary pH class may be referred to as "O" and may correspond to a second predefined pH range of the plurality of predefined pH ranges. In an exemplary embodiment, the pretty low pH class may be referred to as "PL" and may correspond to a third predefined pH range of the plurality of predefined pH ranges. In an exemplary embodiment, the very low pH class may be referred to as "VL" and may correspond to a fourth predefined pH range of the plurality of predefined pH ranges. In an exemplary embodiment, the critically low pH class may be referred to as "CL" and may correspond to a fifth predefined pH range of the plurality of predefined pH ranges.

In an exemplary embodiment, the first predefined pH range may include pH values larger than about 6. In an exemplary embodiment, the second predefined pH range may include pH values between about 5.7 and about 6. In an exemplary embodiment, the third predefined pH range may include pH values between about 5.5 and about 5.7. In an exemplary embodiment, the fourth predefined pH range may include pH values between about 5 and about 5.5. In an exemplary embodiment, the fifth predefined pH range may include pH values smaller than about 5.

In an exemplary embodiment, processor 208 may be utilized to generate the plurality of pH classes by associating a separate class to each of the plurality of predefined pH ranges. For example, a label "N" may be assigned to a pH value that may lie in the first predefined pH range, and a label "O" may be assigned to a pH value that may lie in the second predefined pH range, and so on. TABLE 1 shows each of the plurality of pH classes and corresponding pH ranges.

TABLE 1

The plurality of pH classes and corresponding pH ranges.

| pH class | Approximate pH range |
|---|---|
| N | pH > 6 |
| O | 5.7 < pH < 6 |
| PL | 5.5 < pH < 5.7 |
| VL | 5 < pH < 5.5 |
| CL | pH < 5 |

In further detail with respect to step 112, an exemplary plurality of sodium bicarbonate classes may include a zero sodium bicarbonate class, a low sodium bicarbonate class, a medium sodium bicarbonate class, a high sodium bicarbonate class, and a very high sodium bicarbonate class. In an exemplary embodiment, the zero sodium bicarbonate class may be referred to as "Z" and may correspond to a first predefined sodium bicarbonate mass range of the plurality of predefined sodium bicarbonate mass ranges. In an exemplary embodiment, the low sodium bicarbonate class may be referred to as "L" and may correspond to a second predefined sodium bicarbonate mass range of the plurality of predefined sodium bicarbonate mass ranges. In an exemplary embodiment, the medium sodium bicarbonate class may be referred to as "M" and may correspond to a third predefined sodium bicarbonate mass range of the plurality of predefined sodium bicarbonate mass ranges. In an exemplary embodiment, the high sodium bicarbonate class may be referred to as "H" and may correspond to a fourth predefined sodium bicarbonate mass range of the plurality of predefined sodium bicarbonate mass ranges. In an exemplary embodiment, the very high sodium bicarbonate class may be referred to as "VH" and may correspond to a fifth predefined sodium bicarbonate mass range of the plurality of predefined sodium bicarbonate mass ranges.

In an exemplary embodiment, the first predefined sodium bicarbonate mass range may include zero grams of sodium bicarbonate. In an exemplary embodiment, the second predefined sodium bicarbonate mass range may include values between about 120 gr and about 150 gr of sodium bicarbonate. In an exemplary embodiment, the third predefined sodium bicarbonate mass range may include values between about 150 gr and about 175 gr of sodium bicarbonate. In an exemplary embodiment, the fourth predefined sodium bicarbonate mass range may include values between about 175 gr and about 187 gr of sodium bicarbonate. In an exemplary embodiment, the fifth predefined sodium bicarbonate mass range may include values between about 187 gr and about 200 gr of sodium bicarbonate.

In an exemplary embodiment, processor 208 may be utilized to generate the plurality of sodium bicarbonate classes by associating a separate class to each of the plurality of predefined sodium bicarbonate mass ranges. For example, a label "Z" may be assigned to an amount of sodium bicarbonate that may lie in the first predefined sodium bicarbonate mass range, and a label "L" may be assigned to an amount of sodium bicarbonate that may lie in the second predefined sodium bicarbonate mass range, and so on. TABLE 2 shows each of the plurality of sodium bicarbonate classes and corresponding sodium bicarbonate mass ranges.

TABLE 2

The plurality of sodium bicarbonate classes and corresponding sodium bicarbonate mass ranges.

| Sodium bicarbonate class | Approximate sodium bicarbonate mass range (gr) |
|---|---|
| Z | Zero |
| L | 120-150 |
| M | 150-175 |
| H | 175-187 |
| VH | 187-200 |

For further detail with respect to step 116, in an exemplary embodiment, each rule of the set of rules may include mapping a pair of pH classes to a respective sodium bicarbonate class of the plurality of sodium bicarbonate classes. In an exemplary embodiment, the pair of pH classes may include a first pH class of the plurality of pH classes and a second pH class of the plurality of pH classes. In an exemplary embodiment, the first pH class may be associated with the first average of the pH data and the second pH class may be associated with the second average of the pH. Therefore, in an exemplary embodiment, if the first average is in a predefined pH range corresponding to the first pH class and the second average is in a predefined pH range corresponding to the second pH class (as shown in TABLE 1), the first average and the second average may be mapped to a respective sodium bicarbonate class (as shown in TABLE 2) based on the set of rules, as described below.

For further detail with regards to the set of rules, in an exemplary embodiment, mapping the pair of pH classes to the respective sodium bicarbonate class may include mapping a pair of CL and CL to VH, mapping a pair of CL and VL to VH, mapping a pair of CL and PL to H, mapping a pair of CL and O to M, mapping a pair of CL and N to M, mapping a pair of VL and CL to VH, mapping a pair of VL and VL to H, mapping a pair of VL and PL to M, mapping a pair of VL and O to M, mapping a pair of VL and N to L, mapping a pair of PL and CL to H, mapping a pair of PL and VL to M, mapping a pair of PL and PL to M, mapping a pair of PL and O to L, mapping a pair of PL and N to L, mapping a pair of O and CL to M, mapping a pair of O and VL to L, mapping a pair of O and PL to L, mapping a pair of O and O to L, mapping a pair of O and N to Z, mapping a pair of N and CL to L, mapping a pair of N and VL to Z, mapping a pair of N and PL to Z, mapping a pair of N and O to Z, and mapping a pair of N and N to Z. TABLE 3 summarizes mapping each pair of pH classes to a respective sodium bicarbonate class based on the above-mentioned rules.

TABLE 3

Rules for mapping pairs of pH classes to each of the plurality of sodium bicarbonate classes

| | | Second pH range | | | | |
|---|---|---|---|---|---|---|
| | | CL | VL | PL | O | N |
| First pH range | CL | VH | VH | H | M | Z |
| | VL | VH | H | M | M | L |
| | PL | H | M | M | L | L |
| | O | M | L | L | L | Z |
| | N | L | Z | Z | Z | Z |

Figure 1B:
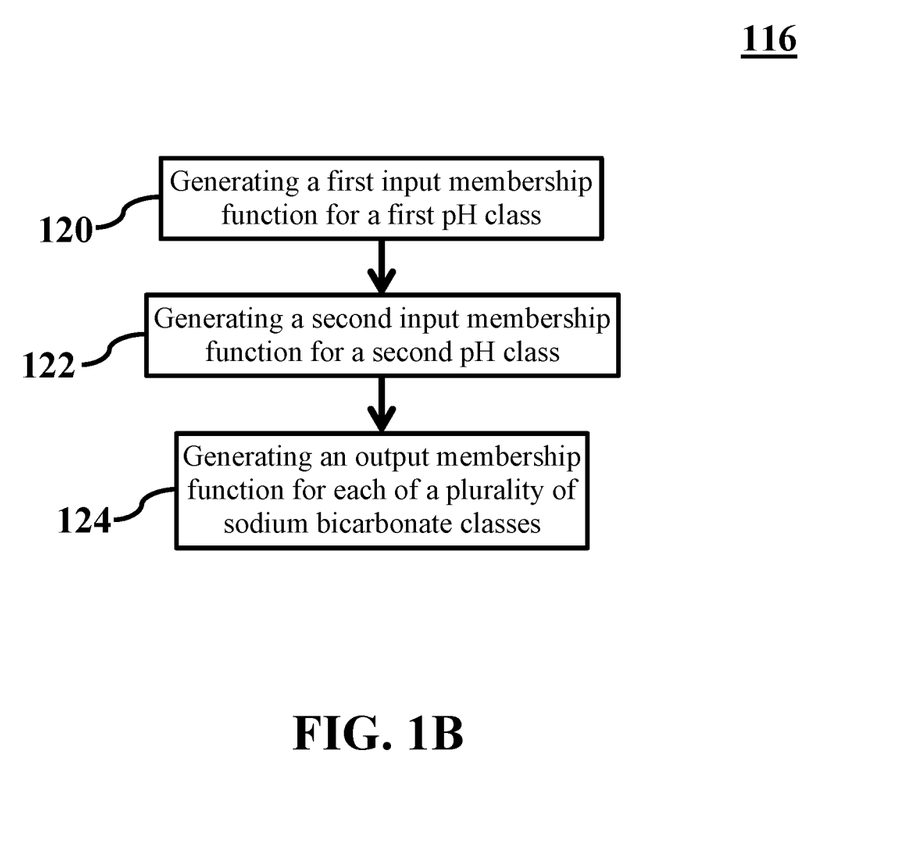
FIG. 1B shows a flowchart of designing a fuzzy control system, consistent with one or more exemplary embodiments of the present disclosure.

FIG. 1B shows a flowchart of designing a fuzzy control system, consistent with one or more exemplary embodiments of the present disclosure. In an exemplary embodiment, designing the fuzzy control system (step 116) may include generating a first input membership function for the first pH class (step 120), generating a second input membership function for the second pH class (step 122), and generating an output membership function for each of the plurality of sodium bicarbonate classes (step 124). In an exemplary embodiment, each of the first input membership function, the second input membership function, and the output membership function may be generated by implementing a respective mathematical formula utilizing processor 208

Figure 3:
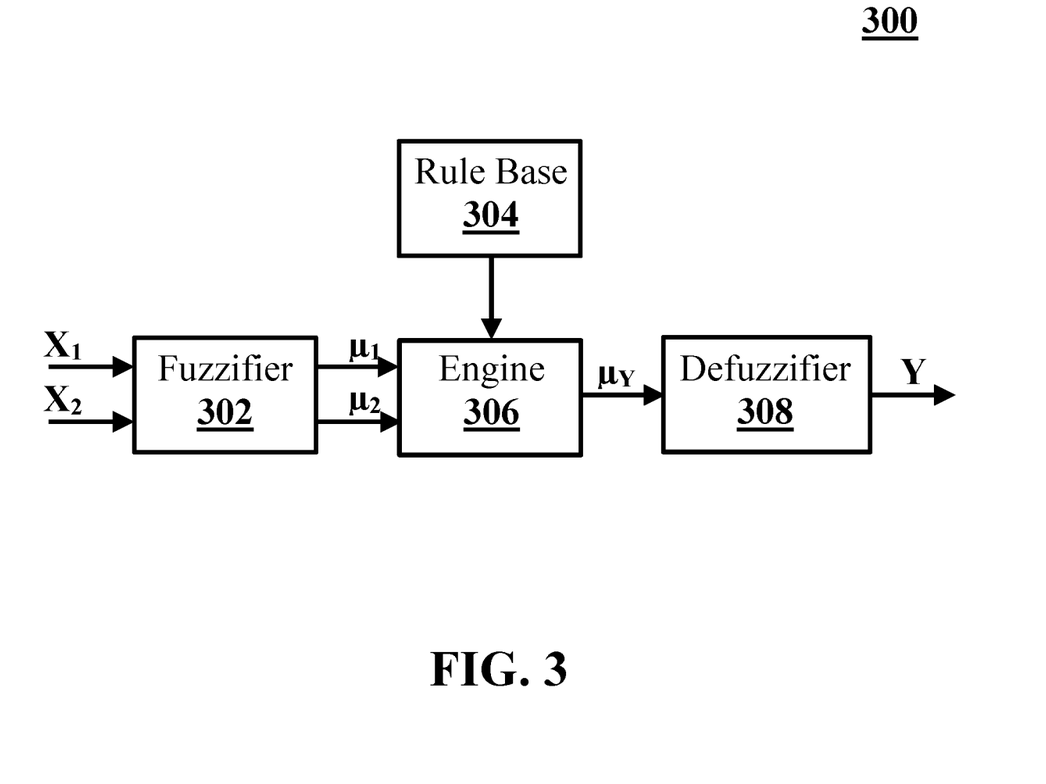
FIG. 3 shows a schematic of a fuzzy control system, consistent with one or more exemplary embodiments of the present disclosure.

FIG. 3 shows a schematic of a fuzzy control system, consistent with one or more exemplary embodiments of the present disclosure. In an exemplary embodiment, processor 208 may be utilized to design a fuzzy control system 300. In an exemplary embodiment, fuzzy control system 300 may include a first input $X_1$, a second input $X_2$, a fuzzifier 302, a fuzzy rule base 304, an inference engine 306, a defuzzifier 308, and an output Y.

In further detail with respect to step 120, in an exemplary embodiment, generating the first input membership function may include mapping first input $X_1$ to a first fuzzy output $\mu_1$. In an exemplary embodiment, fuzzifier 302 may be configured to map first input $X_1$ to first fuzzy output $\mu_1$ utilizing a given formula that may be associated with the first input membership function. As a result, a crisp value of first input $X_1$ may be mapped to a fuzzy value of first fuzzy output $\mu_1$.

For further detail with regards to step 122, in an exemplary embodiment, generating the second input membership function may include mapping second input $X_2$ to a second fuzzy output $\mu_2$. In an exemplary embodiment, fuzzifier 302 may be configured to map second input $X_2$ to second fuzzy output $\mu_2$ utilizing a given formula that may be associated with the second input membership function. As a result, a crisp value of second input $X_2$ may be mapped to a fuzzy value of second fuzzy output $\mu_2$.

In further detail with respect to step 124, in an exemplary embodiment, generating the output membership function may include mapping first fuzzy output $\mu_1$ and second fuzzy output $\mu_2$ to an inferred output $\mu_Y$ utilizing fuzzy rule base 304. In an exemplary embodiment, fuzzy rule base 304 may include the set of rules shown in TABLE 3. In an exemplary embodiment, inference engine 306 may be configured to map first fuzzy output $\mu_1$ and second fuzzy output $\mu_2$ to inferred output $\mu_Y$ utilizing the set of rules that may be stored in fuzzy rule base 304. In an exemplary embodiment, inferred output $\mu_Y$ may be associated with output Y. In an exemplary embodiment, defuzzifier 308 may be configured to map inferred output $\mu_Y$ to output Y. As a result, a fuzzy value of inferred output $\mu_Y$ may be mapped to a crisp value of output Y.

Figure 4:
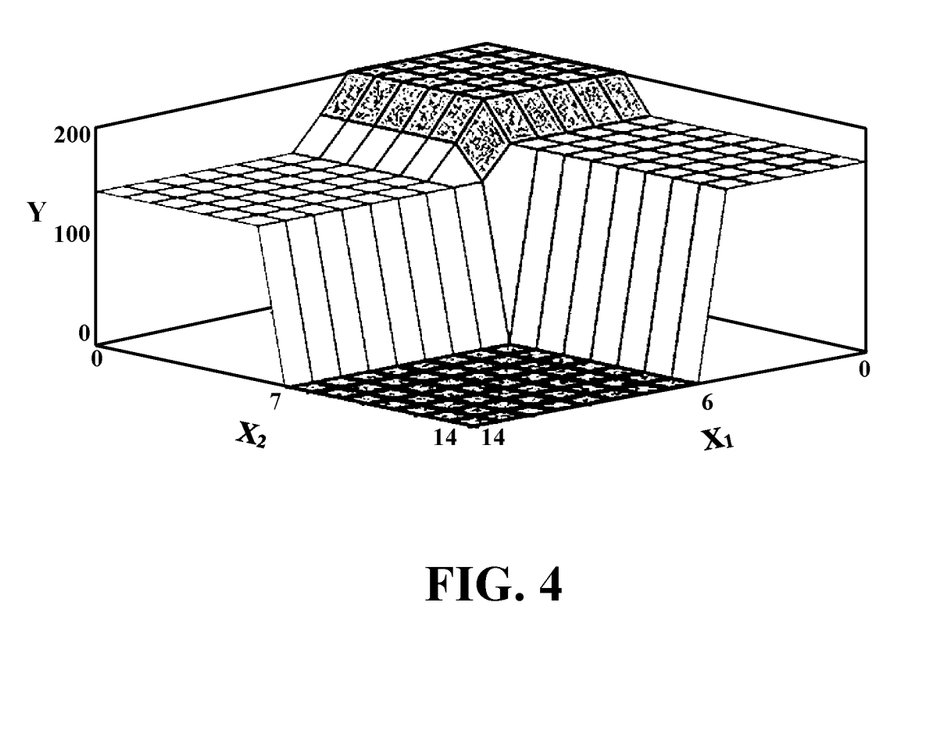
FIG. 4 shows a graphical representation of input-output relationship of a fuzzy control system, consistent with one or more exemplary embodiments of the present disclosure.

In an exemplary embodiment, each of the first input membership function, the second input membership function, and the output membership function may include a trapezoidal shape. FIG. 4 shows a graphical representation of input-output relationship of fuzzy control system 300, consistent with one or more exemplary embodiments of the present disclosure. As shown in FIG. 4, trapezoidal shape membership functions may create a fuzzy relationship between output Y and different pairs of first input $X_1$ and second input $X_2$.

Figure 1C:
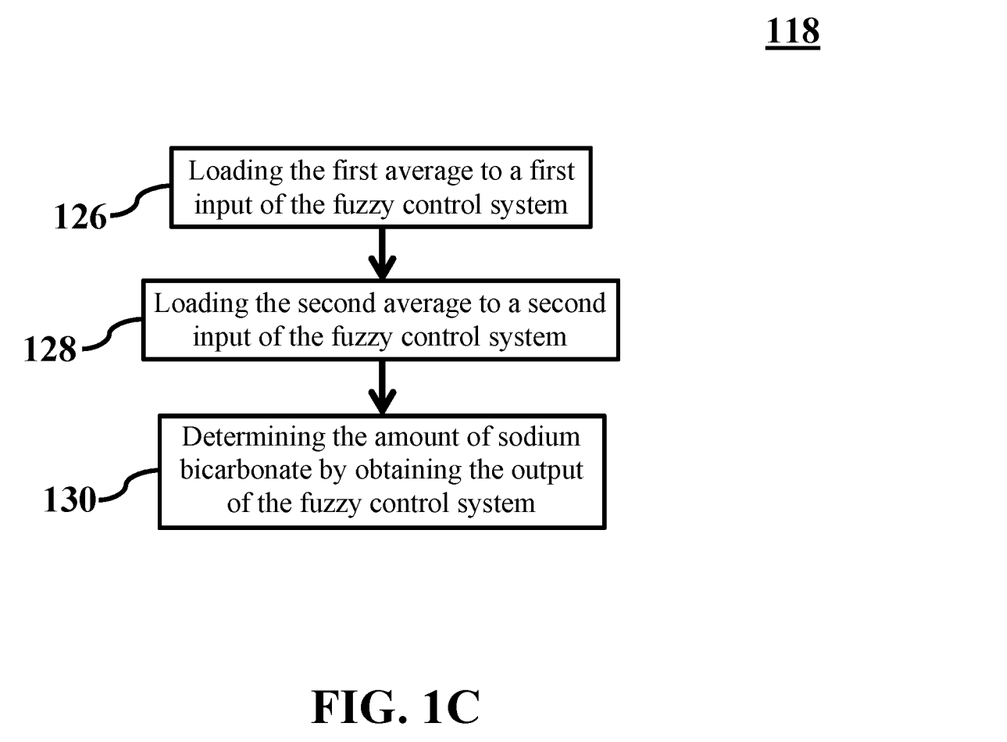
FIG. 1C shows a flowchart of determining an amount of sodium bicarbonate, consistent with one or more exemplary embodiments of the present disclosure.

For further detail with regards to step 118, FIG. 1C shows a flowchart of determining an amount of bicarbonate sodium, consistent with one or more exemplary embodiments of the present disclosure. In an exemplary embodiment, determining the amount of sodium bicarbonates may include loading the first average pH to first input $X_1$ of fuzzy control system 300 (step 126), loading the second average pH to second input $X_2$ of fuzzy control system 300 (step 128), and determining the amount of sodium bicarbonate by obtaining output Y of fuzzy control system 300 (step 130).

In further detail with regards to step 126, step 128, and step 130, in an exemplary embodiment, loading the first average pH to first input $X_1$ and loading the second average pH to second input $X_2$ may cause fuzzy control system 300 to generate an appropriate value for the amount of sodium bicarbonate at output Y based on the set of rules shown in TABLE 3.

Figure 5:
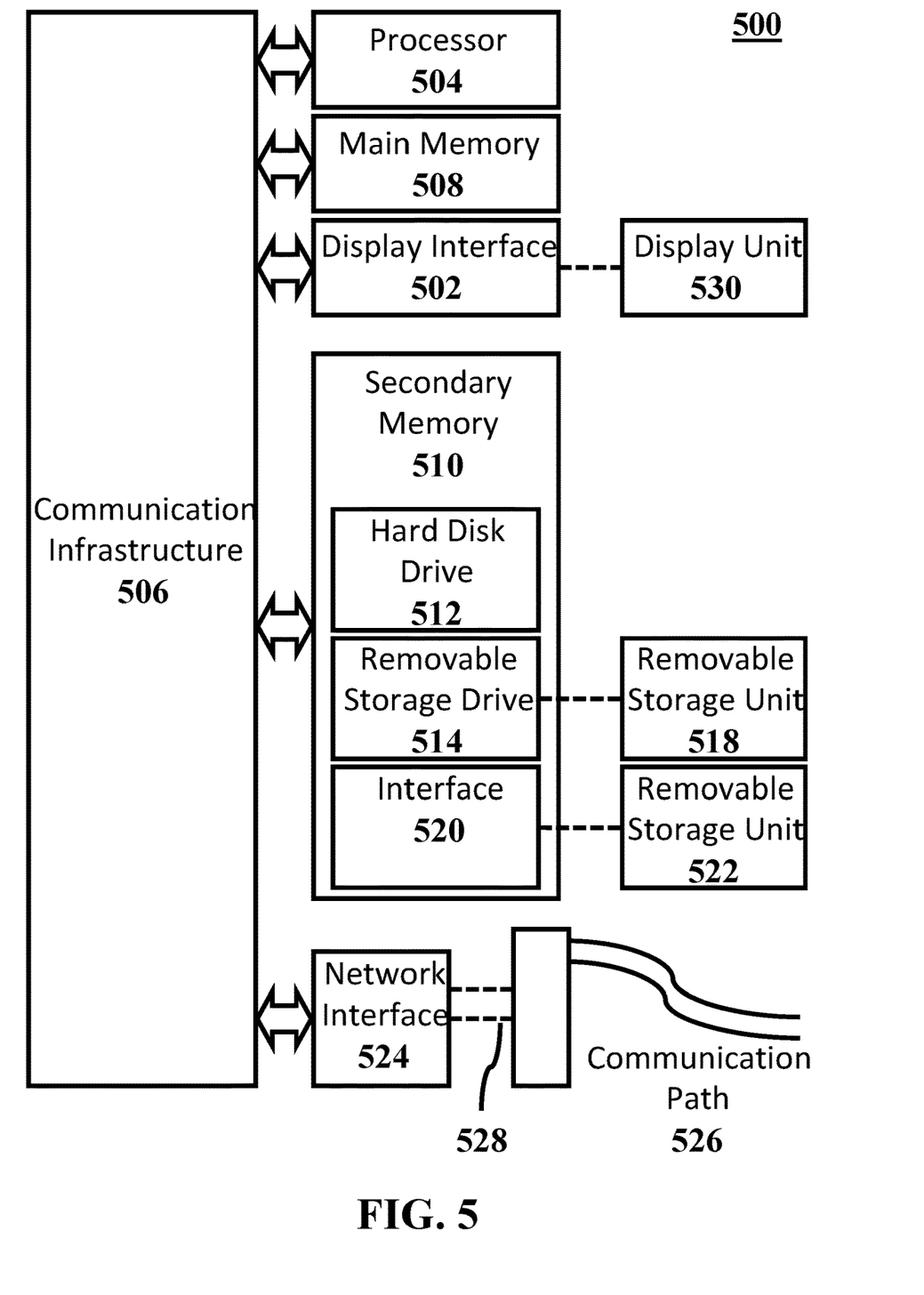
FIG. 5 shows a high-level functional block diagram of a computer system, consistent with one or more exemplary embodiments of the present disclosure.

FIG. 5 shows an example computer system 500 in which an embodiment of the present invention, or portions thereof, may be implemented as computer-readable code, consistent with exemplary embodiments of the present disclosure. For example, method 100 may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-3.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 100 illustrated by flowchart 100 of FIG. 1A, flowchart 116 of FIG. 1B and flowchart 118 of FIG. 1CB discussed above. In an exemplary embodiment, processor device 504 may be analogous to processor 208. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for controlling sub-acute ruminal acidosis (SARA) in a dairy cow, the method comprising:
    placing a pH sensor in a rumen of the dairy cow;
    obtaining pH data of the rumen utilizing the pH sensor;
    receiving the pH data by one or more processors;
    calculating, utilizing the one or more processors, a first average of the pH data and a second average of the pH data, the first average associated with a first period of time and the second average associated with a second period of time;
    generating, utilizing the one or more processors, a plurality of pH classes based on a plurality of predefined pH ranges, each of the plurality of pH classes corresponding to a respective predefined pH range of the plurality of predefined pH ranges;
    generating, utilizing the one or more processors, a plurality of sodium bicarbonate classes based on a plurality of predefined sodium bicarbonate mass ranges, each of the plurality of sodium bicarbonate classes corresponding to a respective predefined sodium bicarbonate mass range of the plurality of predefined sodium bicarbonate mass ranges;
    designing, utilizing the one or more processors, a fuzzy control system based on a set of rules, each rule of the set of rules comprising mapping a pair of pH classes to a respective sodium bicarbonate class of the plurality of sodium bicarbonate classes, the pair of pH classes comprising a first pH class of the plurality of pH classes and a second pH class of the plurality of pH classes, the first pH class associated with the first average and the second pH class associated with the second average, wherein the fuzzy control system comprises a first input, a second input, and an output;
    determining an amount of sodium bicarbonate to add to a water supply of the dairy cow utilizing the fuzzy control system based on the first average and the second average, the determining the amount of sodium bicarbonate comprises:
        loading the first average to the first input of the fuzzy control system;
        loading the second average to the second input of the fuzzy control system; and
        determining the amount of sodium bicarbonate by obtaining the output of the fuzzy control system; and
    compensating SARA in the dairy cow by feeding the amount of sodium bicarbonate to the dairy cow.

2. The method of claim 1, wherein the first period of time comprises a 24 hour period.

3. The method of claim 2, wherein the second period of time comprises a 5 hour period.

4. The method of claim 1, wherein generating the plurality of pH classes comprises:
    generating a normal pH class (N) corresponding to a first predefined pH range of the plurality of predefined pH ranges, the first predefined pH range comprising pH values larger than 6;
    generating an ordinary pH class (O) corresponding to a second predefined pH range of the plurality of predefined pH ranges, the second predefined pH range comprising pH values between 5.7 and 6;
    generating a pretty low pH class (PL) corresponding to a third predefined pH range of the plurality of predefined pH ranges, the third predefined pH range comprising pH values between 5.5 and 5.7;
    generating a very low pH class (VL) corresponding to a fourth predefined pH range of the plurality of predefined pH ranges, the fourth predefined pH range comprising pH values between 5 and 5.5; and
    generating a critically low pH class (CL) corresponding to a fifth predefined pH range of the plurality of predefined pH ranges, the fifth predefined pH range comprising pH values smaller than 5.

5. The method of claim 4, wherein generating the plurality of sodium bicarbonate classes comprises:
    generating a zero sodium bicarbonate class (Z) corresponding to a first predefined sodium bicarbonate mass range of the plurality of predefined sodium bicarbonate mass ranges, the first predefined sodium bicarbonate mass range comprising zero grams of sodium bicarbonate;
    generating a low sodium bicarbonate class (L) corresponding to a second predefined sodium bicarbonate mass range of the plurality of predefined sodium bicarbonate mass ranges, the second predefined sodium bicarbonate mass range comprising values between 120 gr and 150 gr of sodium bicarbonate;
    generating a medium sodium bicarbonate class (M) corresponding to a third predefined sodium bicarbonate mass range of the plurality of predefined sodium bicarbonate mass ranges, the third predefined sodium bicarbonate mass range comprising values between 150 gr and 175 gr of sodium bicarbonate;
    generating a high sodium bicarbonate class (H) corresponding to a fourth predefined sodium bicarbonate mass range of the plurality of predefined sodium bicarbonate mass ranges, the fourth predefined sodium bicarbonate mass range comprising values between 175 gr and 187 gr of sodium bicarbonate; and
    generating a very high sodium bicarbonate class (VH) corresponding to a fifth predefined sodium bicarbonate mass range of the plurality of predefined sodium bicarbonate mass ranges, the fifth predefined sodium bicarbonate mass range comprising values between 187 gr and 200 gr of sodium bicarbonate.

6. The method of claim 5, wherein mapping the pair of pH classes to the respective sodium bicarbonate class comprises:
    mapping a pair of CL and CL to VH;
    mapping a pair of CL and VL to VH;
    mapping a pair of CL and PL to H;
    mapping a pair of CL and O to M;
    mapping a pair of CL and N to M;
    mapping a pair of VL and CL to VH;
    mapping a pair of VL and VL to H;
    mapping a pair of VL and PL to M;
    mapping a pair of VL and O to M;
    mapping a pair of VL and N to L;
    mapping a pair of PL and CL to H;
    mapping a pair of PL and VL to M;
    mapping a pair of PL and PL to M;
    mapping a pair of PL and O to L;
    mapping a pair of PL and N to L;
    mapping a pair of O and CL to M;
    mapping a pair of O and VL to L;
    mapping a pair of O and PL to L;
    mapping a pair of O and O to L;
    mapping a pair of O and N to Z;

mapping a pair of N and CL to L;
mapping a pair of N and VL to Z;
mapping a pair of N and PL to Z;
mapping a pair of N and O to Z; and
mapping a pair of N and N to Z.

7. The method of claim 1, wherein designing the fuzzy control system comprises:
generating a first input membership function for the first pH class, the first input membership function associated with the first input;
generating a second input membership function for the second pH class, the second input membership function associated with the second input; and
generating an output membership function for each of the plurality of sodium bicarbonate classes, the output membership function associated with the output.

8. The method of claim 7, wherein generating each of the first input membership function, the second input membership function, and the output membership function comprises generating a trapezoidal function.

9. A system for controlling sub-acute ruminal acidosis (SARA) in a dairy cow, the system comprising:
a pH sensor placed in a rumen of the dairy cow, the pH sensor configured to obtain pH data of the rumen;
a transmitter coupled with the pH sensor, the transmitter configured to transmit the pH data;
a receiver configured to receive the pH data from the transmitter;
a memory having processor-readable instructions stored therein, the memory configured to receive the pH data from the receiver; and
a processor configured to access the memory and execute the processor-readable instructions, which, when executed by the processor configures the processor to perform a method, the method comprising:
calculating a first average of the pH data and a second average of the pH data, the first average associated with a first period of time and the second average associated with a second period of time;
generating a plurality of pH classes based on a plurality of predefined pH ranges, each of the plurality of pH classes corresponding to a respective predefined pH range of the plurality of predefined pH ranges;
generating a plurality of sodium bicarbonate classes based on a plurality of predefined sodium bicarbonate mass ranges, each of the plurality of sodium bicarbonate classes corresponding to a respective predefined sodium bicarbonate mass range of the plurality of predefined sodium bicarbonate mass ranges;
designing a fuzzy control system based on a set of rules, each rule of the set of rules comprising mapping a pair of pH classes to a respective sodium bicarbonate class of the plurality of sodium bicarbonate classes, the pair of pH classes comprising a first pH class of the plurality of pH classes and a second pH class of the plurality of pH classes, the first pH class associated with the first average and the second pH class associated with the second average, wherein the fuzzy control system comprises a first input, a second input, and an output, wherein designing the fuzzy control system comprises:
generating a first input membership function for the first pH class, the first input membership function associated with the first input;
generating a second input membership function for the second pH class, the second input membership function associated with the second input; and
generating an output membership function for each of the plurality of sodium bicarbonate class, the output membership function associated with the output,
wherein each of the first input membership function, the second input membership function, and the output membership function comprises a trapezoidal shape;
determining an amount of sodium bicarbonate to add to a water supply of the dairy cow utilizing the fuzzy control system based on the first average and the second average; and
compensating SARA in the dairy cow by feeding the amount of sodium bicarbonate to the dairy cow.

10. The system of claim 9, wherein the first period of time comprises a 24 hour period.

11. The system of claim 10, wherein the second period of time comprises a 5 hour period.

12. The system of claim 9, wherein generating the plurality of pH classes comprises:
generating a normal pH class (N) corresponding to a first predefined pH range of the plurality of predefined pH ranges, the first predefined pH range comprising pH values larger than 6;
generating an ordinary pH class (O) corresponding to a second predefined pH range of the plurality of predefined pH ranges, the second predefined pH range comprising pH values between 5.7 and 6;
generating a pretty low pH class (PL) corresponding to a third predefined pH range of the plurality of predefined pH ranges, the third predefined pH range comprising pH values between 5.5 and 5.7;
generating a very low pH class (VL) corresponding to a fourth predefined pH range of the plurality of predefined pH ranges, the fourth predefined pH range comprising pH values between 5 and 5.5; and
generating a critically low pH class (CL) corresponding to a fifth predefined pH range of the plurality of predefined pH ranges, the fifth predefined pH range comprising pH values smaller than 5.

13. The system of claim 12, wherein generating the plurality of sodium bicarbonate classes comprises:
generating a zero sodium bicarbonate class (Z) corresponding to a first predefined sodium bicarbonate mass range of the plurality of predefined sodium bicarbonate mass ranges, the first predefined sodium bicarbonate mass range comprising zero grams of sodium bicarbonate;
generating a low sodium bicarbonate class (L) corresponding to a second predefined sodium bicarbonate mass range of the plurality of predefined sodium bicarbonate mass ranges, the second predefined sodium bicarbonate mass range comprising values between 120 gr and 150 gr of sodium bicarbonate;
generating a medium sodium bicarbonate class (M) corresponding to a third predefined sodium bicarbonate mass range of the plurality of predefined sodium bicarbonate mass ranges, the third predefined sodium bicarbonate mass range comprising values between 150 gr and 175 gr of sodium bicarbonate;
generating a high sodium bicarbonate class (H) corresponding to a fourth predefined sodium bicarbonate mass range of the plurality of predefined sodium bicarbonate mass ranges, the fourth predefined sodium bicarbonate mass range comprising values between 175 gr and 187 gr of sodium bicarbonate; and generating a very high sodium bicarbonate class (VH) corresponding to a fifth predefined sodium bicarbonate mass range of the plurality of predefined sodium bicarbonate mass ranges, the fifth predefined sodium bicarbonate mass range comprising values between 187 gr and 200 gr of sodium bicarbonate.

14. The system of claim 13, wherein mapping the pair of pH classes to the respective sodium bicarbonate class comprises:

mapping a pair of CL and CL to VH;
mapping a pair of CL and VL to VH;
mapping a pair of CL and PL to H;
mapping a pair of CL and O to M;
mapping a pair of CL and N to M;
mapping a pair of VL and CL to VH;
mapping a pair of VL and VL to H;
mapping a pair of VL and PL to M;
mapping a pair of VL and O to M;
mapping a pair of VL and N to L;
mapping a pair of PL and CL to H;
mapping a pair of PL and VL to M;
mapping a pair of PL and PL to M;
mapping a pair of PL and O to L;
mapping a pair of PL and N to L;
mapping a pair of O and CL to M;
mapping a pair of O and VL to L;
mapping a pair of O and PL to L;
mapping a pair of O and O to L;
mapping a pair of O and N to Z;
mapping a pair of N and CL to L;
mapping a pair of N and VL to Z;
mapping a pair of N and PL to Z;
mapping a pair of N and O to Z; and
mapping a pair of N and N to Z.

15. The system of claim 9, wherein determining the amount of sodium bicarbonate comprises:

loading the first average to the first input of the fuzzy control system;
loading the second average to the second input of the fuzzy control system; and
determining the amount of sodium bicarbonate by obtaining the output of the fuzzy control system.

* * * * *